United States Patent
Das et al.

(10) Patent No.: US 9,823,232 B2
(45) Date of Patent: Nov. 21, 2017

(54) LIGAND FOR DETECTION OF CHROMIUM (III) AND A PROCESS FOR THE PREPARATION THEREOF

(71) Applicant: COUNCIL OF SCIENTIFIC & INDUSTRIAL RESEARCH, New Delhi (IN)

(72) Inventors: Amitava Das, Pune (IN); Firoj Ali, Pune (IN); Sukdeb Saha, Bhavnager (IN)

(73) Assignee: COUNCIL OF SCIENTIFIC & INDUSTRIAL RESEARCH, New Delhi (IN)

(*) Notice: Subject to any disclaimer, the term of this patent is extended or adjusted under 35 U.S.C. 154(b) by 0 days.

(21) Appl. No.: 15/028,272

(22) PCT Filed: Oct. 8, 2014

(86) PCT No.: PCT/IN2014/000646
§ 371 (c)(1),
(2) Date: Apr. 8, 2016

(87) PCT Pub. No.: WO2015/052731
PCT Pub. Date: Apr. 16, 2015

(65) Prior Publication Data
US 2016/0252488 A1    Sep. 1, 2016

(30) Foreign Application Priority Data
Oct. 8, 2013    (IN) .......................... 2991/DEL/2013

(51) Int. Cl.
| | |
|---|---|
| *C07D 491/107* | (2006.01) |
| *G01N 33/20* | (2006.01) |
| *G01N 33/52* | (2006.01) |
| *C09B 11/24* | (2006.01) |
| *C09B 11/26* | (2006.01) |
| *G01N 21/64* | (2006.01) |
| *G01N 33/58* | (2006.01) |
| *G01N 33/84* | (2006.01) |

(52) U.S. Cl.
CPC .......... *G01N 33/20* (2013.01); *C07D 491/107* (2013.01); *C09B 11/24* (2013.01); *C09B 11/26* (2013.01); *G01N 21/643* (2013.01); *G01N 21/6428* (2013.01); *G01N 33/52* (2013.01); *G01N 33/582* (2013.01); *G01N 33/84* (2013.01); *G01N 2021/6439* (2013.01)

(58) Field of Classification Search
CPC ................................................ C07D 491/107
See application file for complete search history.

(56) References Cited

PUBLICATIONS

Lei, et al. Document No. 157:147444, retrieved from STN; entered in STN on Aug. 9, 2011.*

M.H. Lee et al.: "Metal Ion Induced Fret Off-On in Tren/Dansyl-Appended Rhodamine", Organic Letters, vol. 10, No. 2 Dec. 14, 2007 (Dec. 14, 2007), pp. 213-216, XP002734475.

Y. Lei et. al.: "Photophysical property of rhodamine-cored poly(amidoamine) dendrimers. Simultaneous effect of spirolactam ring-opening and PET process on sensing trivalent chromium ion.", Journal of Liuminescence vol. 131, Jul. 16, 2011 (Jul. 16, 2011), pp. 2521-2527, XP002734476, p. 2525, col. 1, paragraph 2—p. 2526, col. 2, paragraph 1; figures 1-6.

Z. Zhou et. al,: "FRET Based Sensor for Imaging Chormium(III) in Living Cells.", Chemical Communications, vol. 2008, May 23, 2008 (May 23, 2008) pp. 3387-3389, XP002734477, DOI: 10.1039/b801503a.

J. Mao et. al.: "Tuning the selectivity of Two Chemosensors to Fe(III) and Cr(III).", Organic Letters, vol. 9, No. 22, Sep. 27, 2007 (Sep. 27, 2007), pp. 4567-4570, XP002734478.

J. Mao et. al. : "An "On-Off" Fluorescense Probe for Chromium (III) Ion Determination in Aqueous Solution.", Analytical and Bioanalytical Chemistry, vol. 396, Dec. 22, 2009 (Dec. 22, 2009), pp. 1197-1203, XP002734479.

Feb. 20, 2015—International Search Report and Written Opinion for PCT/IN2014/000646.

X.Wan et al., "A Stimuli-Responsive Nanogel-Based Sensitive and Selective FluorescentSensor for Cr3+ with Thermo-induced Tunable Detection Sensitivity" Macromolecular Rapid Communications, 2014 24 323.

D. Wang, et al., "A distyryl BODIPY derivative as a fluorescent probe for selective detection of chromium(III)" , Tetrahedron Letters 51 (2010) 2545.

* cited by examiner

*Primary Examiner* — Shawquia Jackson
(74) *Attorney, Agent, or Firm* — Banner & Witcoff, Ltd.

(57) ABSTRACT

The invention disclosed herein relates to novel ligands (Lx) of Formula-I for selective detection of Cr (III) in pure aqueous medium and industrially viable process for the preparation thereof. Further the invention provides the process of selective detection of Cr (III) by fluorimetry using novel ligands of Formula-I. The invention also discloses a method of solubilizing novel ligands of formula-I in pure aqueous medium with the aid of non-ionic surfactant. The invention discloses a method of selective detection of Cr (III) using novel ligands of Formula-I.

Formula-I (Lx)

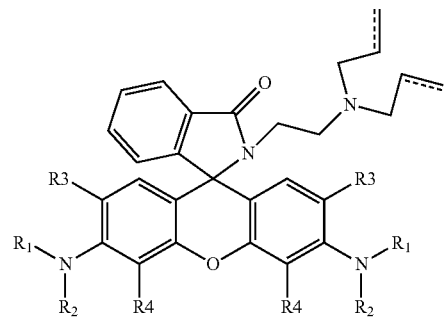

8 Claims, 8 Drawing Sheets

LIGAND FOR DETECTION OF CHROMIUM (III) AND A PROCESS FOR THE PREPARATION THEREOF

CROSS-REFERENCE TO RELATED APPLICATIONS

The present application is a U.S. National Phase filing of International Application No. PCT/IN2014/000646, filed on Oct. 8, 2014, designating the United States of America and claiming priority to Indian Patent Application No. 2991/DEL/2013 filed Oct. 8, 2013, and the present application claims priority to and the benefit of both the above-identified applications, which are incorporated by reference herein in their entireties.

FIELD OF THE INVENTION

The invention discloses a novel ligand ($L_x$) of Formula-I with high selectivity to Cr (III) and a process for the preparation thereof. Particularly, the invention further discloses a method of determining Cr (III) in fluids, where the ligand should have solubility in aqueous medium with the aid of non-ionic surfactant.

Formula-I (Lx)

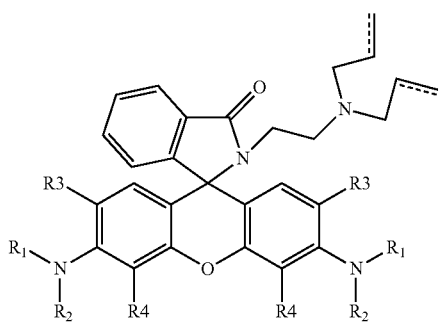

BACKGROUND AND PRIOR ART OF THE INVENTION

Due to its high paramagnetic behavior it is challenging for chemists to develop fluorogenic receptors specific for Cr (III) detection with fluorescence on response, as it is well known to quench the luminescence of a fluorophore. Further, due to the high solvation enthalpy of Cr (III)-ion in aqueous medium, it is also difficult to find an appropriate receptor for Cr(III-ion that works in pure aqueous medium.

There are only few examples of receptors available in the literature, which binds exclusively to Cr (III) in an ensemble of several other competing metal ions. The Receptor 1 was reported by Li et. al, Chem. commun, 2008, 3387. It is a FRET based chemo sensor for detection of Cr(III) in ethanol/water (2/1, v/v) medium and it can be used as an imaging agent in HeLa cell.

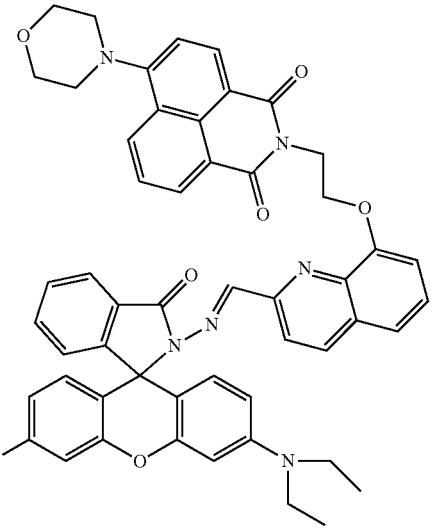

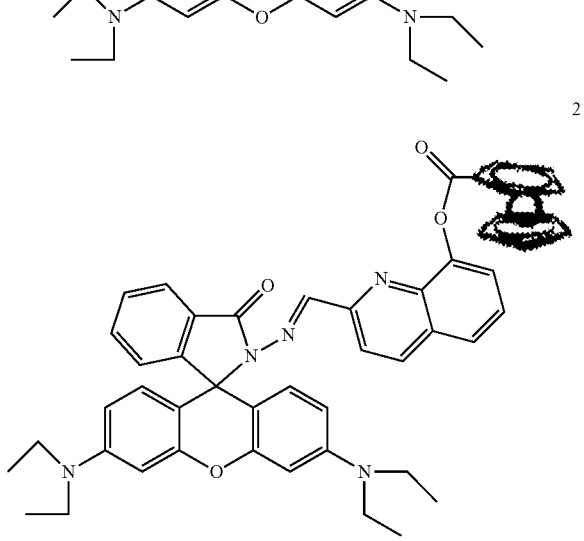

Li et at also reported another Ferrocene Based Receptor 2 (*Org. lett,* 2008, 2557) for selective detection of Cr(III) in ethanol/water (1/1, v/v) with an association constant of $7.5 \times 10^3$ $M^{-1}$. Receptors 3 (Anal. Methods, 2012, 3163; receptor is effective in acetonitrile/water (9/1, v/v)) and 4 (Anal. Methods, 2012, 2254; receptor is effective in methanol/water (9/1, v/v)) were developed by D. Das and his co-workers and both reagents showed high selectivity towards Cr(III) in predominantly organic medium. Receptor 5 is a BODIPY based Cr(III) sensors synthesised by D. Wang et al. (Tetrahedron Letters, 2010, 51, 2545). It can detect Cr(III) selectively in acetonitrite with binding stoichiometry of 2:2.

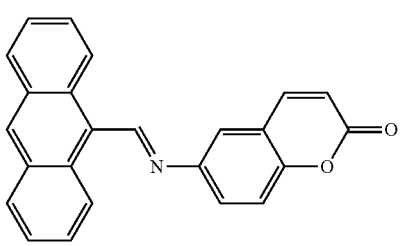

-continued

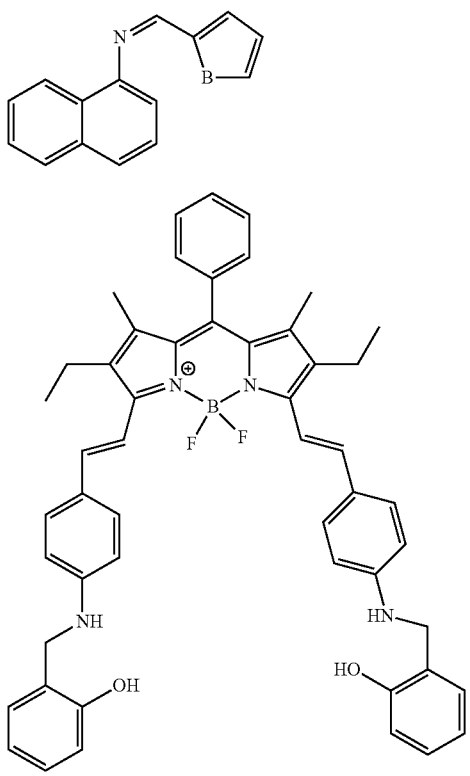

Further Hassan S S, et al. in *Analytical Sciences (Impact Factor:* 1.57). July 2005; 21(6):673-8 discloses use of a rhodamine-B chromate ion-associate complex as an electroactive material in a poly(vinyl chloride) membrane plasticized with o-nitrophenyloctyl ether as a solvent mediator. It is to be noted that the oxidation state for Chromium in chromate is (VI). They reported a Potentiometric Rhodamine B based Membrane Sensor for selective determination of Chromium ions [Cr(VI) & Cr(III)] in waste water. Firstly it can't detect Cr(III) directly. To detect Cr(III) they have adopted an indirect methodology in which Cr(III) was first oxidised to Cr(VI) by adding $H_2O_2$, that can be sensed by the reported sensor. Another important thing, this types of sensors cannot be applied for bio imaging application to monitor intra cellular Cr(III) activity.

In the present invention $L_1$ it can selectively detect only Cr(III) in pure aqueous medium. It does not have any interferences of Cr(VI) at all. It is a fluoromertic as well as colorimetric sensor for Cr(III) detection. It can be used for monitoring intra cellular imaging of Cr(III). Fluorescence detection methods are more sensitive and simpler compare to other analytical methods.

Highly sensitive and selective fluorescence chemosensor for $Cr^{3+}$ based on rhodamine B and a 4,13-diaza-18-crown 6-ether conjugate" is disclosed by Duliang Liu, in *RSC Adv.,* 26 Nov. 2013, 4, 2563-2567, where detection of $Cr^{3+}$ was possible only in predominantly non aqueous environment (3:2, MeOH—$H_2O$ (v/v).

There are only three previous reports that describe the use of reagents for the detection of Cr(III) in pure aqueous solution; (Mao, J et al. *Org. Lett.,* 2007, 9, 4567-4570 and Mao, J et al. *Anal. Bioanal. Chem.,* 2010, 396, 1197) one of them describes the interference by $Fe^{3+}$. The most recent report reveals that a rhodamine derivative within a polymeric matrix could be utilized for specific detection of Cr (III) in pure aqueous medium and the hydrophobic microenvironment generated around the binding core of the receptor induces a favourable influence for the detection of Cr(III) (*Macromol. Rapid Commun.* 2014, 35, 323) However, the possibility of using these three molecular probes as an imaging reagent for studying the cellular uptake of Cr(III) is not explored and discussed.

While the receptors disclosed herein have the capability to detect Cr (III) in pure aqueous medium and in physiological condition. All other above examples suffer from a major drawback that they have this capability of detecting Cr (III) only in mixed aqueous organic solvents medium.

Detection of Cr (III) in pure aqueous solution is a very basic and vital need in the art, so that Cr(III) may be monitored for its presence and activity in cellular structure. There is also a need to detect Cr (III) in physiological fluids.

OBJECTS OF THE INVENTION

Main objective of the present invention is to provide a novel ligand that could selectively detects Cr (III) in aqueous medium as well as in physiological pH (7.2).

Another objective of the invention is to develop a methodology for solubilizing the reagent in pure aqueous medium in presence of non-ionic surfactant like Titron X 100.

SUMMARY OF THE INVENTION

Accordingly, the present invention provides novel ligands of Formula I (Lx) for detection of Chromium in pure aqueous medium Formula I

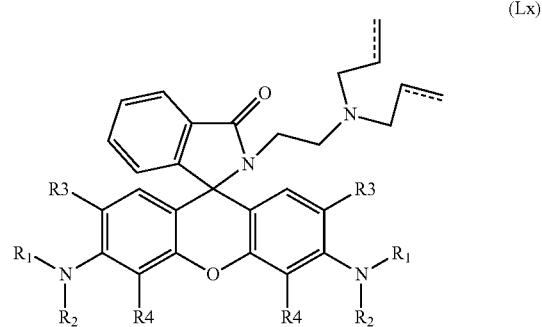

(Lx)

wherein $R_1$ and $R_2$ are same or different and individually selected from the group consisting of H, linear or branched (C1-C6) alkyl, aryl or dansyl; R3 is same selected from group H, methyl; R4 is selected from H, (C1-C6) alkyl; where, R1 may form saturated or unsaturated carbocyclic (C4-C6) ring with R3 and similarly R2 may form saturated or unsaturated carbocyclic (C4-C6) ring with R4; and ( . . . ) line is optionally represents single bond.

In one embodiment of the present invention the ligand of formula-I, encompasses the compounds selected from the group consisting of;

L₁ 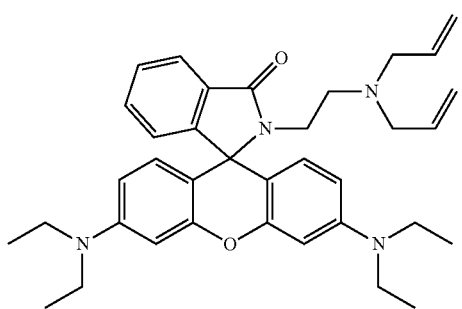

L₂ 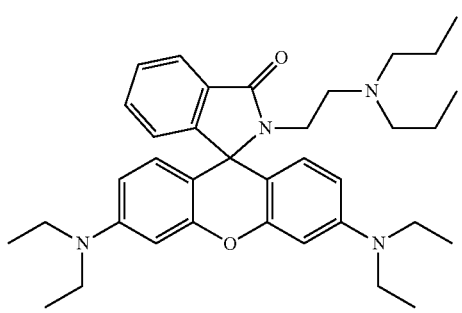

L₃ 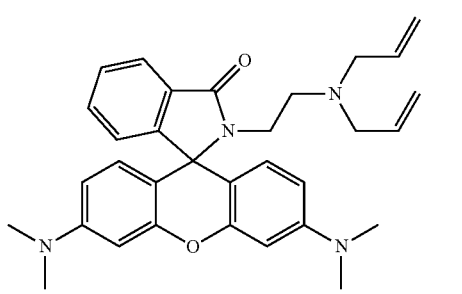

L₄ 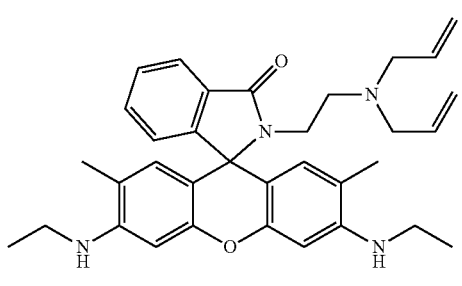

L₅ 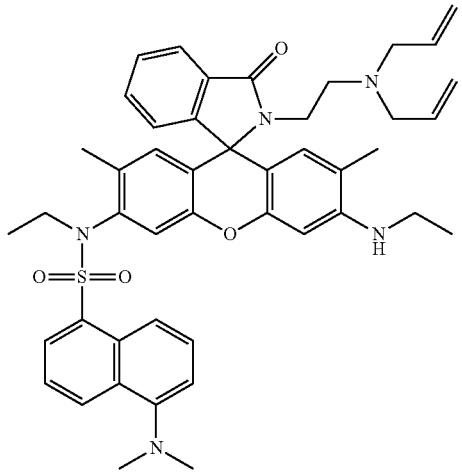

L₆ 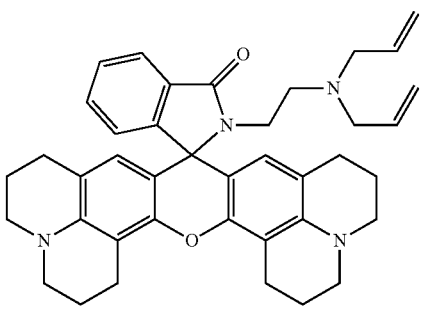

In an embodiment of the present invention a process of preparation of ligands of Formula I (Lx), wherein the said process comprising the steps of:
a. refluxing ethylene diamine and rhodamine B derivatives (II) in organic solvent, to obtain the corresponding amino ethylene rhodamine derivative (III) and;
b. refluxing the amino ethylene rhodamine derivative of step (a) in the presence of (A-Br) aliphatic bromide, triethyl amine and dry $CHCl_3$ under inert conditions to obtain Ligand ($L_x$) of Formula-I.

II 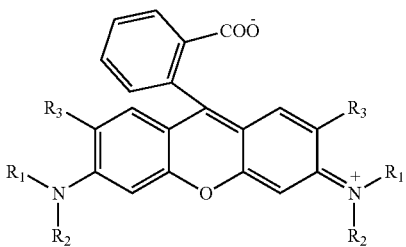

III 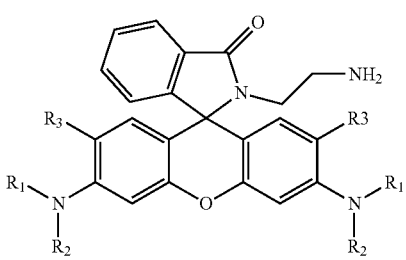

wherein $R_1$ and $R_2$ are same or different and individually selected from the group consisting of H, linear or branched (C1-C6) alkyl, aryl or dansyl; R3 is same selected from group H, methyl;
wherein, R1 may form saturated or unsaturated carbocyclic (C4-C6) ring with R3.

In another embodiment of the present invention the organic solvent is polar organic solvent selected from the group consisting of methanol, isopropanol, n-propanol, ethanol, water, butanol and mixtures thereof.

Still In another embodiment of the present invention the aliphatic bromide (A-Br) is alkene bromide selected from the group consisting of allyl bromide, 3-bromoprop-1-ene or alkyl bromide selected from the group consisting of propyl bromide, 1-bromopropane.

Still In another embodiment of the present invention a process for selective detection of Cr (111) using ligands of Formula-I, in aqueous medium as well as in physiological Liquid of pH (7.2) comprising steps of:

a. preparing a solution of tris(hydroxymethyl)aminomethane buffer (Tris buffer) and Polyethylene glycol tert-octylphenyl ether (Triton X 100) at pH 7.2;
b. preparing a stock solution of ligands of Formula-I in a water miscible solvent in concentration ranges from 6.0 to $8.0 \times 10^{-4}$ M;
c. mixing solution of step (b) with the solution of step (a) to solubilize ligand of formula I;
d. preparing Chromium (III) metal stock solution using water;
e. adding metal solution gradually to the solution of step (c) and;
f. recording spectrum in a UV or fluorescence spectrometer.

Still In another embodiment of the present invention the water miscible solvent is selected from acetonitrile, Methanol, DMSO, Ethanol, THF, DMF and mixtures thereof.

Still In another embodiment of the present invention a kit for selective detection of Cr (III) using novel ligands of Formula-I, comprising
a) Ligand $L_1$ stock solution ($6.9 \times 10^{-4}$ M) in acetonitrile;
b) 0.32 mM Triton X 100 in Tris buffer solution at pH 7.2;
c) Aqueous Cr(III) solution ($3.28 \times 10^{-3}$M);
d) Final ligand solution ($1.59 \times 10^{-5}$ M) in 0.32 mM Triton X 100 in Tris buffer having solution pH of 7.2.

DETAILED DESCRIPTION OF THE INVENTION

Figure 1:
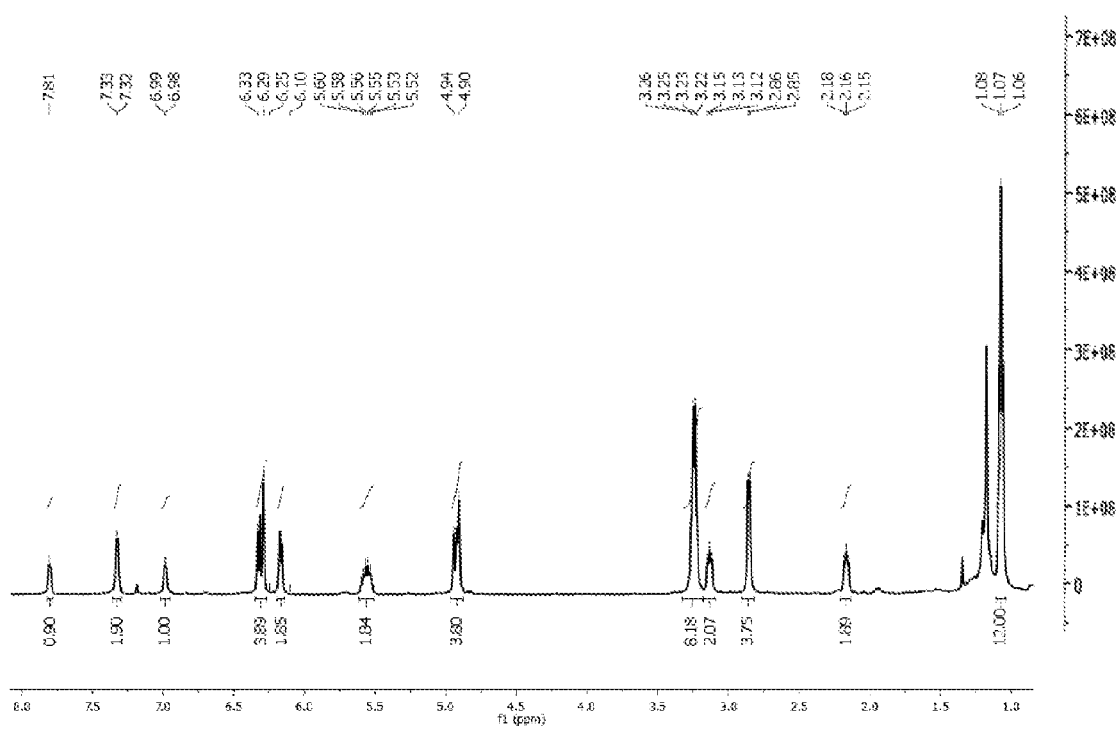
FIG. 1 depicts $^1$H NMR Spectra of ligand $L_1$
Figure 2:
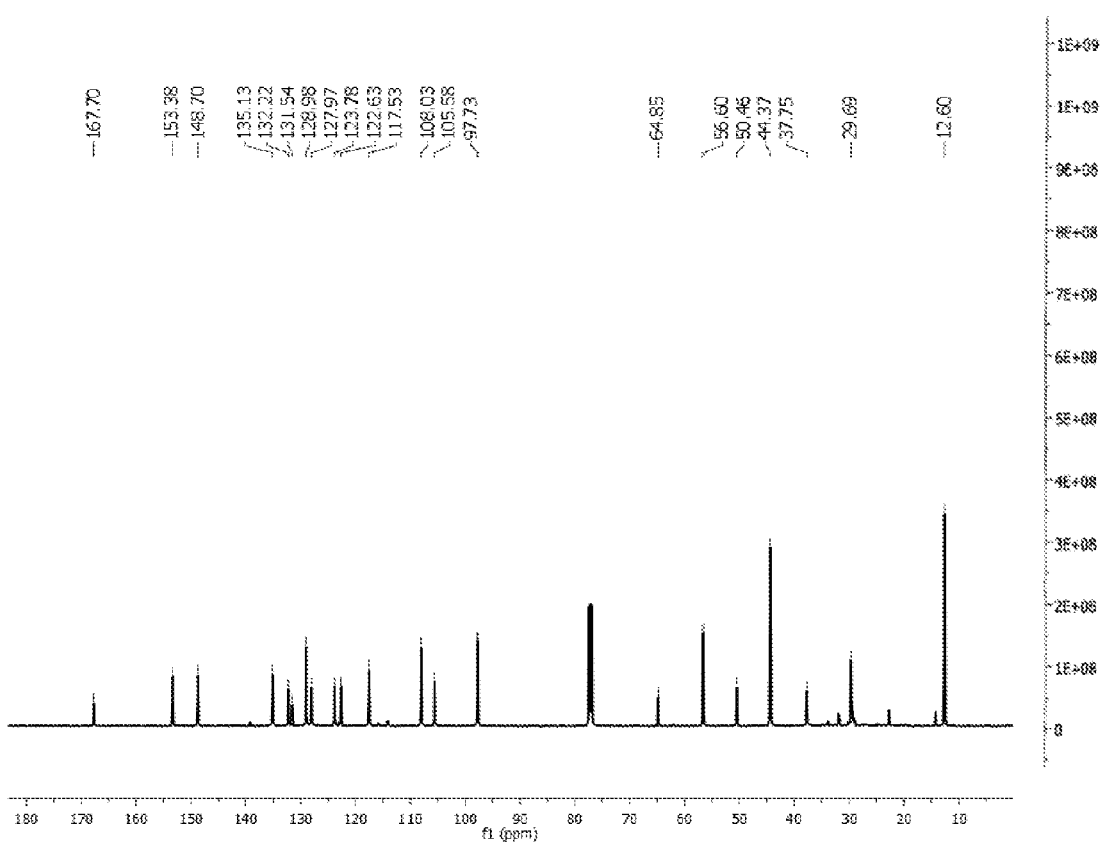
FIG. 2 depicts $^{13}$C NMR of $L_1$

The invention will now be described in detail in connection with certain preferred and optional embodiments, so that various aspects thereof may be more fully understood and appreciated.

For the purpose of this invention, the expression 'Novel Ligand (Lx)' or 'novel reagent' or 'receptor' 'colorimetric' as well as 'fluorescent chemosensor' are used interchangeably throughout the specification and the same may be appreciated as such by the person skilled in the art.

The present invention discloses a novel ligand for selective detection of Cr (III) in aqueous medium.

The novel ligand ($L_x$) of Formula I is as disclosed herein:

Formula I

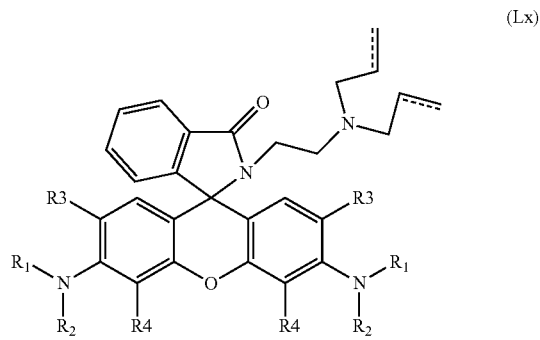

(Lx)

wherein $R_1$ and $R_2$ are same or different and individually selected from the group consisting of H, linear or branched (C1-C6) alkyl, aryl or dansyl; R3 is same selected from group H, methyl; R4 is selected from H, (C1-C6) alkyl;

where, R1 may form saturated or unsaturated carbocyclic (C4-C6) ring with R3 and similarly R2 may form saturated or unsaturated carbocyclic (C4-C6) ring with R4; and ( . . . ) line is optionally represents single bond.

In another preferred embodiment, the invention provides the library of compounds of Formula-I.

The novel ligand (Lx) of Formula-I encompasses the compounds selected from the group consisting of;

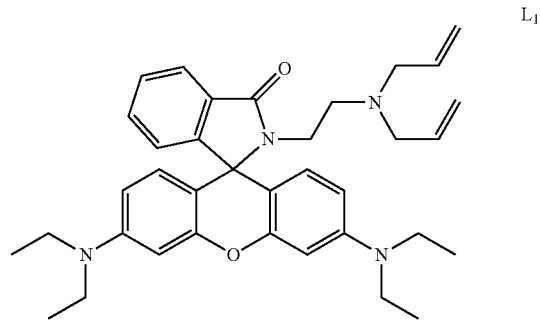

$L_1$

L₂
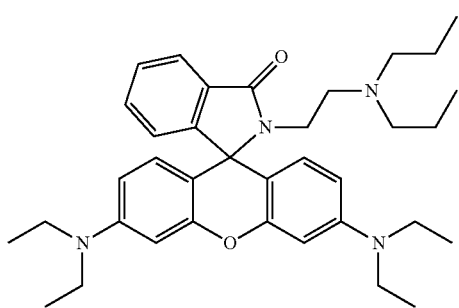

L₃
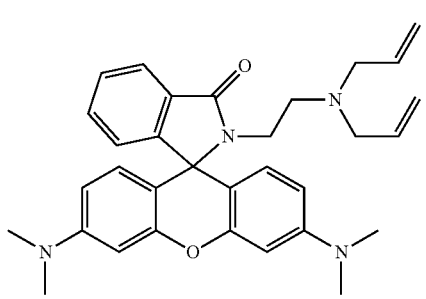

L₄
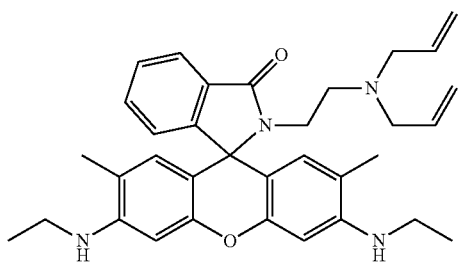

L₅
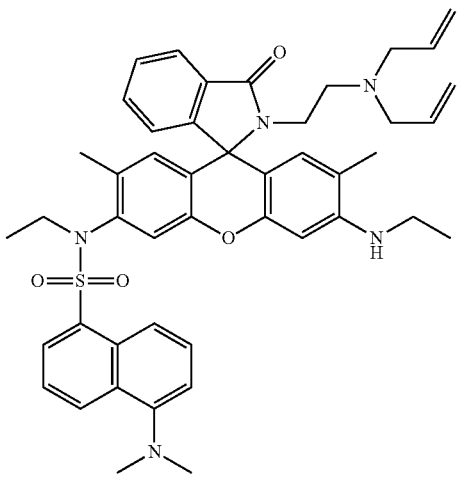

L₆
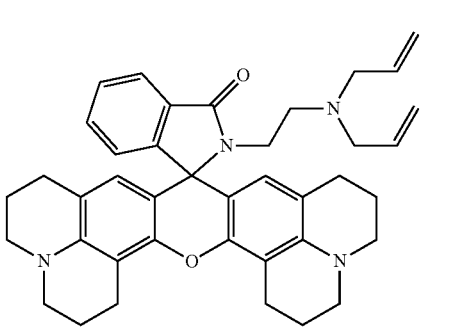

The invention provides a process of preparation of novel ligands of Formula I (Lx) comprising steps of:
a. refluxing ethylene diamine and rhodamine B derivatives (II) in an organic solvent, to obtain the corresponding amino ethylene rhodamine derivative (III) and;
b. refluxing the amino ethylene rhodamine derivative of step (a) in the presence of (A-Br) aliphatic bromide, triethyl amine and dry CHCl₃ under inert conditions to obtain Ligand L_x of Formula-I in good yield. (cf scheme 1)

Scheme 1:

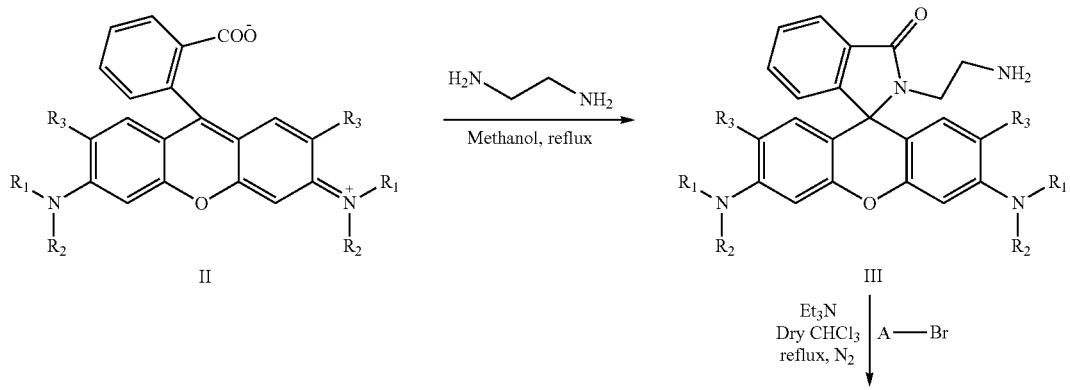

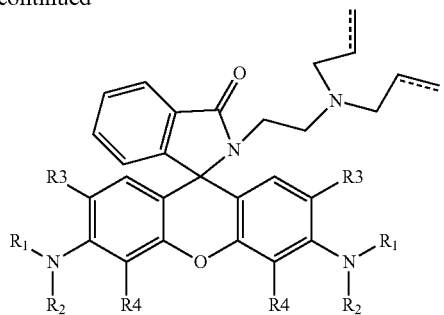

According to the process, the organic solvent is polar organic solvent selected from the group consisting of methanol, isopropanol, n-propanol, ethanol, water, butanol and mixtures thereof.

The aliphatic bromide (A-Br) is preferably alkene or alkyl bromide such as, allyl bromide, propyl bromide, 1-bromopropane, 3-bromoprop-1-ene.

The said process is time saving due to fewer steps and industrially feasible. The invention provides a process of preparation of novel ligands ($L_1$) and ($L_2$) comprising steps of:

a. refluxing ethylene diamine and rhodamine B in methanol to obtain the corresponding amino ethylene rhodamine derivative (L); and
b. refluxing the amino ethylene rhodamine derivative of step (a) in the presence of allyl bromide, triethyl amine and dry $CHCl_3$ under inert conditions to obtain novel Ligand $L_1$; or
c. refluxing the amino ethylene rhodamine derivative of step (a) in the presence of propyl bromide, triethyl amine and dry $CHCl_3$ under inert conditions to obtain novel Ligand $L_2$. (refer scheme 2)

According to the process, the Intermediate compound L was synthesized following a literature procedure, (A. Org. Lett. 2008, 10, 3013-3016). Methodologies that were adopted for synthesis of the receptor $L_1$ and the model compound $L_2$ are presented in the scheme 2. Desired compound $L_1$ and $L_2$ were isolated in pure form after necessary workup and were thoroughly characterized by various analytical/spectroscopic techniques.

The invention discloses a process for solubilisation of ligand $L_1$ in an aqueous medium employing non ionic surfactant, preferably Polyethylene glycol tert-octylphenyl ether (Triton X 100).

Figure 5:
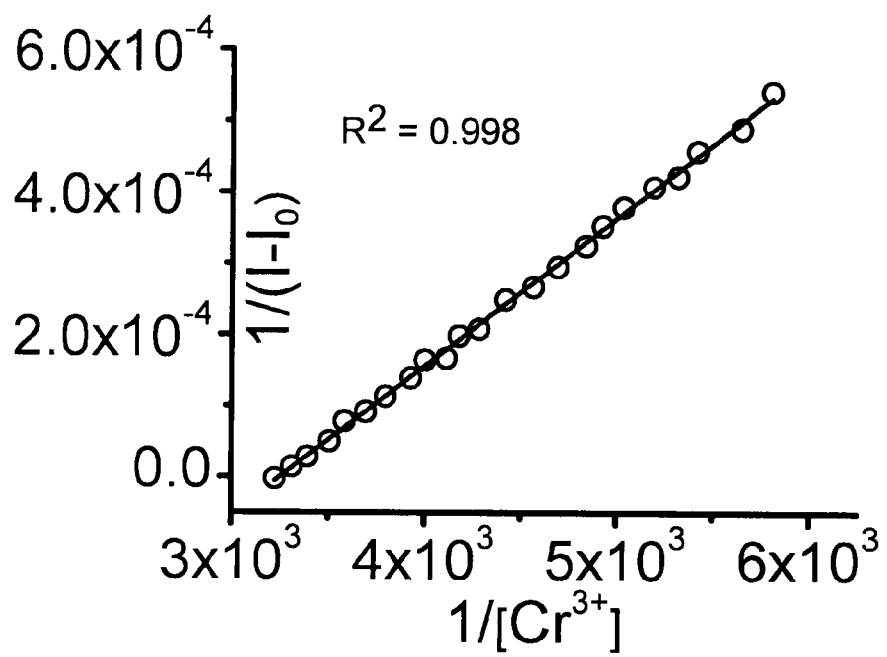
FIG. 5: Benesi-Hildebrand (B-H) plots of emission spectral titration. All studies were performed in aq. solution of 0.4 mM Triton X-100 and Tris buffer (5 mM, 25 mM NaCl; pH 7.2).
Figure 7:
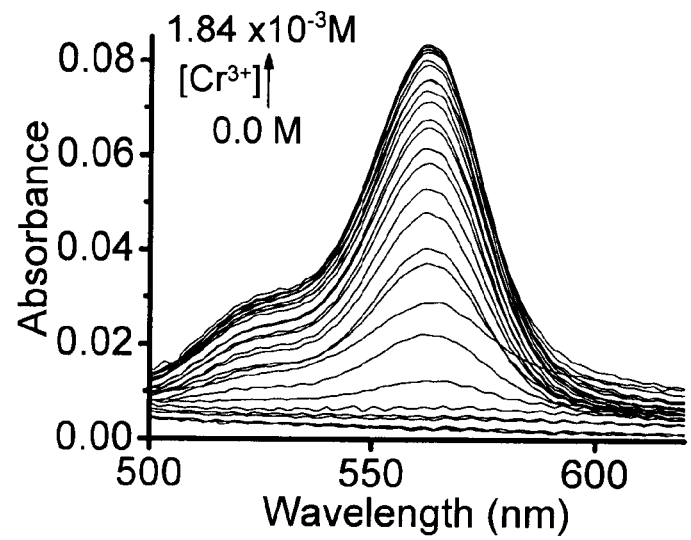
FIG. 7 depicts UV Titration of Ligand $L_1$ ($1.59 \times 10^{-5}$ M) upon addition of aqueous Cr (III) solution in (0.4) mM Triton X 100 in Tris buffer having solution pH 7.2
Figure 8:
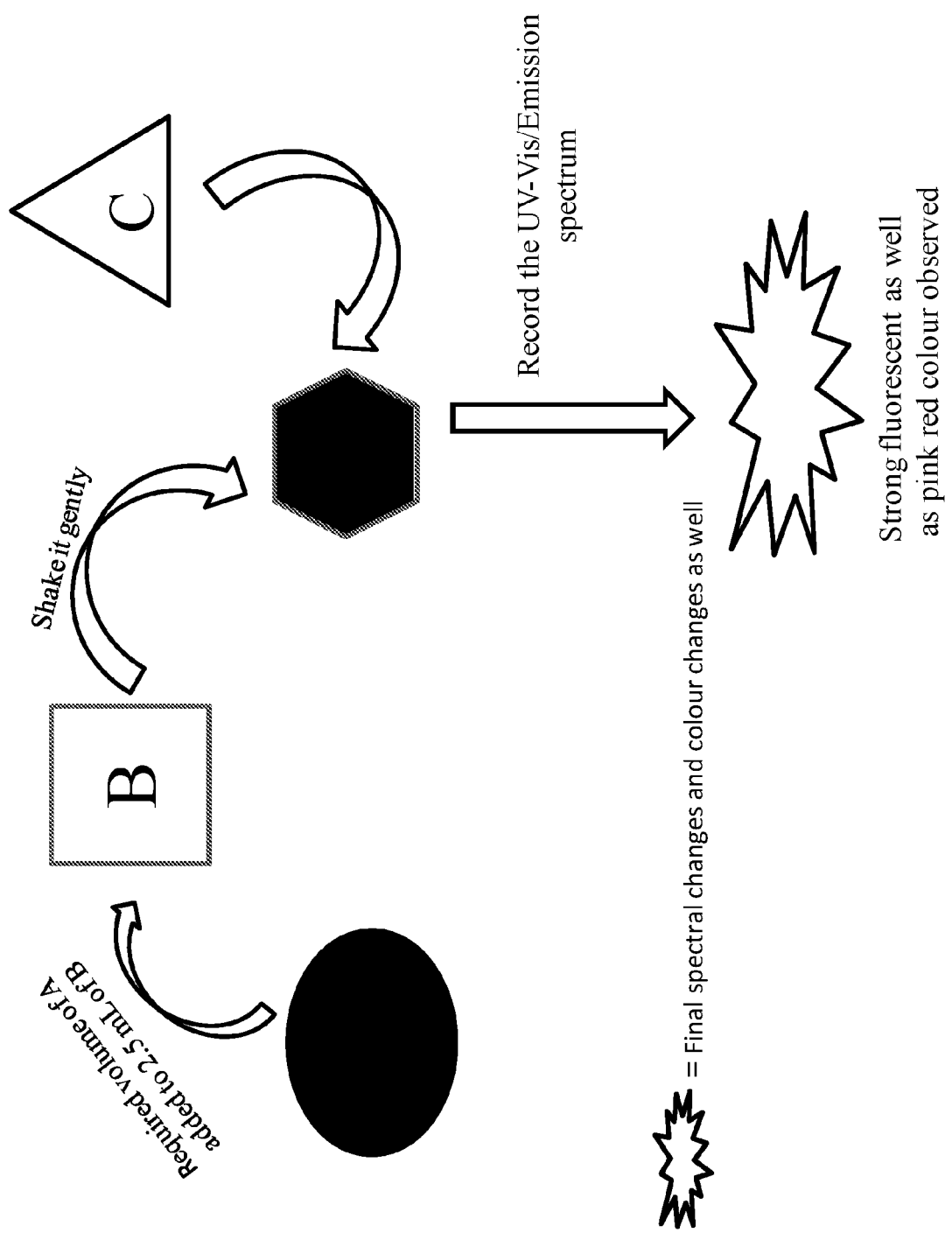
FIG. 8: depicts Flow Chart for detection procedure from a kit
Figure 9:
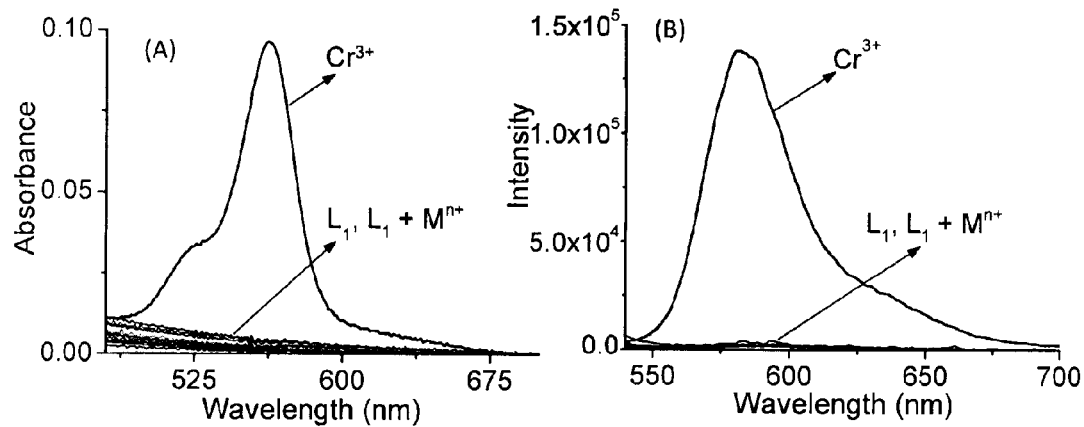
FIG. 9: depicts Changes in (A) absorption and (B) emission spectra ($\lambda_{Ext}$ of 530 nm) of the receptor $L_1$ ($1.59 \times 10^{-5}$ M) in absence and presence of different metal ions ($M^{n+}$: $1.62 \times 10^{-4}$M: $Li^+$, $Na^+$, $K^+$, $Cs^+$, $Ca^{2+}$, $Mg^{2+}$, $Sr^{2+}$, $Ba^{2+}$, $Cr^{3+}$, $Fe^{2+}$, $Co^{3+}$, $Ni^{2+}$, $Cu^{2+}$, $Zn^{2+}$, $Hg^{2+}$, $Cd^{2+}$ and $Pb^{2+}$); All studies were performed in aq. solution of 0.4 mM TX100 and Tris buffer (5 mM, 25 mM NaCl; pH 7.2).
Figure 10:
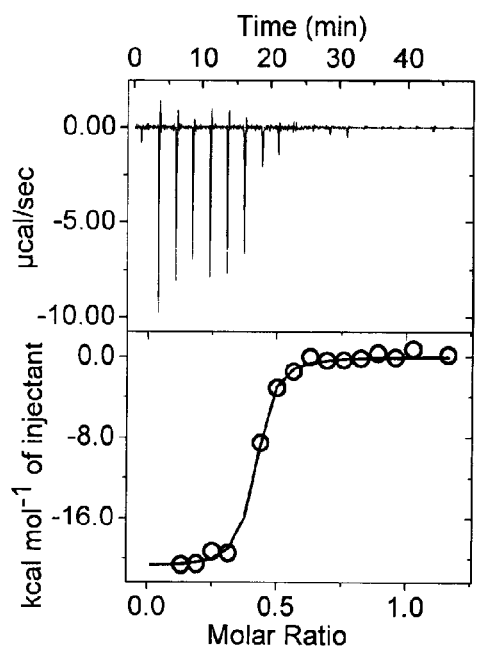
FIG. 10 depicts Isothermal Titration Calorimetry (ITC) titration profile for the binding of $Cr^{3+}$ to receptor $L_1$ at 25° C. in acetonitrile; Top plot: raw data for the sequential 2 μl injection of $Cr^{3+}$ ($1.2 \times 10^{-3}$ M) into solution of $L_1$ ($2.0 \times 10^{-4}$ M) and bottom plot of the heat evolved (kcal per mole) of $Cr^{3+}$ added.

With reference to FIG. 5 & FIG. 7, Ligand $L_1$, dissolved in pure aqueous medium with the aid of Triton X 100, is selective/specific for Cr (III) and excludes similar metals selected from alkali, alkaline earth metals and all common transition metals.

In another preferred embodiment, the alkali, alkaline earth metals and transition metals are selected from, but not limited to Li, Na, K, Cs, Mg, Ca, Ba, Sr, Zn, Co, Cu, Ni, Fe, Pb, Hg and such like.

Scheme 2: (A) Methodology adopted for synthesis of $L_1$ and $L_2$. (B) molecular structure for $Cr^{3+}.L_1$.

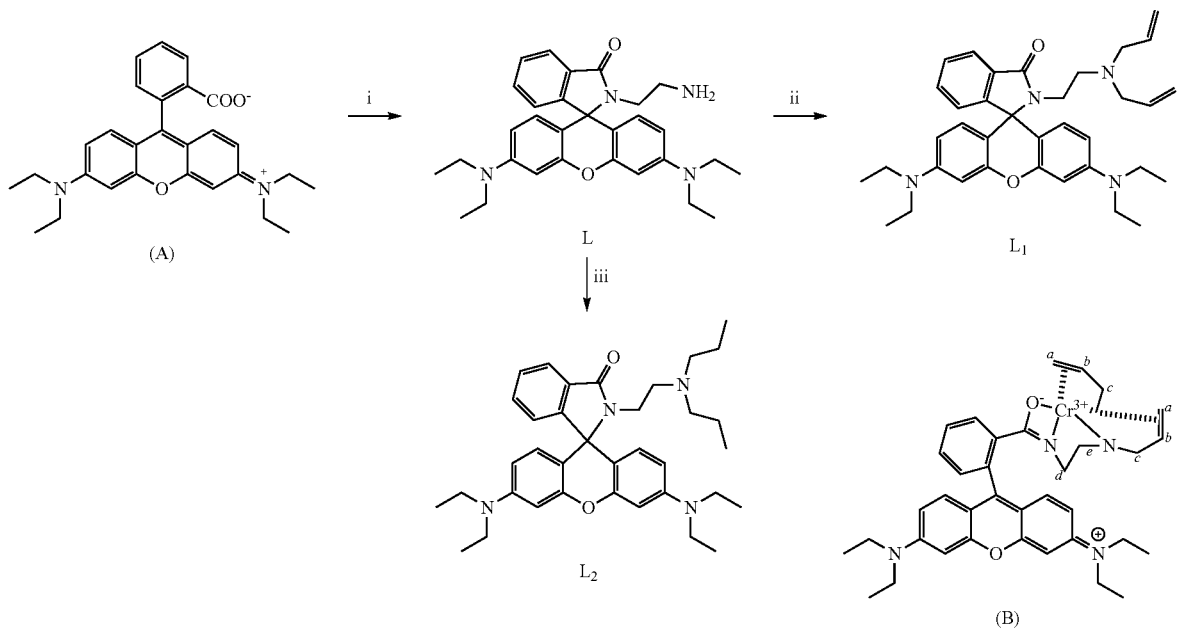

i. $H_2NCH_2CH_2NH_2$, MeOH. Reflux
ii. Dry $CHCl_3$, $H_2C=CHCH_2Br$, $Et_3N$, Inert Atmosphere.
iii. Dry $CHCl_3$, $H_2CCH_2CH_2Br$, $Et_3N$, Inert Atmosphere In another embodiment, the invention discloses the process of selective detection of Cr (III) by a process of fluorimetry comprising:
a. preparing a solution of Tris (tris(hydroxymethyl)aminomethane buffer) buffer and Triton X 100 at pH 7.2;
b. preparing a stock solution Ligand $L_1$ in a water miscible solvent; add required volume of Ligand stock solution to make desired Ligand $L_1$ concentration;
c. mixing Ligand $L_1$ solution of step (b) with the solution of step (a);
d. preparing metal stock solution using water;
e. adding metal solution gradually to the solution of step (c) and;
f. recording spectrum in a UV or fluorescence spectrometer.

According to the process the water miscible solvent is selected from acetonitrile, Methanol, DMSO, Ethanol, THF, DMF and mixtures thereof.

According to the process a stock solution of the receptor/ligand $L_1$ was prepared in acetonitrile medium with concentration ranges from 6.0 to $8.0 \times 10^{-4}$ M, preferably ($6.9 \times 10^{-4}$ M); and the final concentration of metal salts is in the range of 1.0 to $2.0 \times 10^{-4}$ M, preferably $1.62 \times 10^{-4}$ M.

The UV-vis spectrum for the ligand $L_1$ may be carried out from for the range 250-800 nm and a $\lambda_{max}$ of 562 nm is observed. The luminescence studies were carried out using an excitation wavelength of 530 nm and emission spectrum was monitored from 540 to 800 nm, with slit width of 2/2 nm; while a spectrum with $\lambda_{max}$ of 583 nm is observed.

The invention provides a kit for selective detection of Cr (III) is disclosed. a kit for selective detection of Cr (III) comprises:
a) Ligand $L_1$ stock solution in acetonitrile.
b) 0.32 mM Triton X 100 in Tris buffer solution at pH 7.2.
c) Aqueous Cr (III) solution ($3.28 \times 10^{-3}$ M).
d) Final ligand solution ($1.59 \times 10^5$ M) in (0.4) mM Triton X 100 in Tris buffer having solution pH of 7.2.

It describes the method of detection of Cr(III) in an aqueous medium

Further the invention provides a method of separation Cr (III) selectively from a sample comprising other metals, or other ingredients employing the ligand of Formula I described herein. It is possible to extract Cr (III) from aqueous solution when the concentration of Cr (III) either equal to or higher than $8.0 \times 10^{-4}$ M. For extraction studies, dichloromethane ($CH_2Cl_2$) was used as the water immiscible organic solvent for extraction of Cr (III) from aqueous layer in the form of $L_1 \cdot Cr^{3+}$.

Experimental
Materials and Method

Rhodamine B, Ethylenediamine, 3-bromoprop-1-ene, 1-bromopropane, all metal perchlorate salts (e.g $LiClO_4$, $NaClO_4$, $KClO_4$, $CsClO_4$, $Mg(ClO_4)_2$, $Ca(ClO_4)_2$, $Ba(ClO_4)_2$, $Sr(ClO_4)_2$, $Cu(ClO_4)_2$, $Zn(ClO_4)_2$, $Co(ClO_4)_2$, $Ni(ClO_4)_2$, $Cr(ClO_4)_3$, $Fe(ClO_4)_2$, $Cd(ClO_4)_2$, $Hg(ClO_4)_2$, and $Pb(ClO_4)_2$) and lanthanide ions as nitrate salts were obtained from Sigma-Aldrich and were used as received. $Et_3N$, Triton X-100, Tris Buffer, NaCl was procured from S.D. fine chemicals, India and was used as received. Solvents such as acetonitrile, chloroform were also purchased from S.D. Fine Chemicals, India and were used without further purification unless mentioned otherwise. Silica gel 100-200 mesh was used for column chromatography. Analytical thin layer chromatography was performed using silica Gel GF 254. HPLC grade water (Merck, India) was used for experiments and all spectral studies. Aminoethylene rhodamine B (L) was synthesized following a standard procedure (*Org. Lett.* 2008, 10, 3013-3016)

5.0 mM Tris-HCl aq. buffer solution was used for maintaining solution pH, unless mentioned otherwise. ESI-MS measurements were performed using a Micromass QTof-Micro instrument. FT-IR spectra were recorded as KBr pellets using a Perkin Elmer Spectra GX 2000 spectrometer. $^1H$ and $^{13}C$ NMR spectra were recorded on Bruker 500 MHz FT NMR (model: Avance-DPX 500). Electronic spectra were recorded with a Varian Cary 500 Scan UV-Vis-NIR Spectrophotometer, Isothermal Titration Calorimetry studies were performed in Microcal iTC200, while emission spectra were recorded using either Edinburgh Instrument Xe-900 Spectrofluorometer or PTI. For all spectroscopic studies in aqueous buffer medium as well as for studies with plant/algal cells, $L_1$ self-assembled inside the miceller structure of TX100 was used, unless mentioned otherwise.

Photophysical Study:

To check the selectivity of Receptor $L_1$ towards various metal ions like $Li^+$, $Na^+$, $K^+$, $Cs^+$, $Mg^{2+}$, $Ca^{2+}$, $Ba^{2+}$, $Sr^{2+}$, $Zn^{2+}$, $Co^{3+}$, $Cu^{2+}$, $Ni^{2+}$, $Fe^{2+}$, $Pb^{2+}$, $Hg^{2+}$ change in electronic as well as emission spectra were examined in 0.32 mM Triton X 100 in tris (5 mM, 25 mM NaCl) buffer medium at PH 7.2.

Absorption and emission spectra of receptor $L_1$ in 0.32 mM Triton X 100 in Tris buffer (5 mM, 25 mM NaCl) pH 7.2 medium shows no absorption band at 562 nm and very weak emission band at 583 nm on excitation at 562 nm. This solution of $L_1$ appears colourless and all these clearly suggest that $L_1$ in this solution is present exclusively in spirolactam form. This is also confirmed from the $^{13}C$ NMR studies, which shows a characteristic signal at 64.85 ppm for the tertiary C-atom. However only in presence of $Cr^{3+}$, a strong absorption band at 562 nm and intense emission band at 583 nm (for $\lambda_{ext}$=530 nm) are observed. These changes are also associated with simultaneous visually detectable change in solution colour from colourless to pink red. For other metal ions, no such changes are observed.

Figure 3:
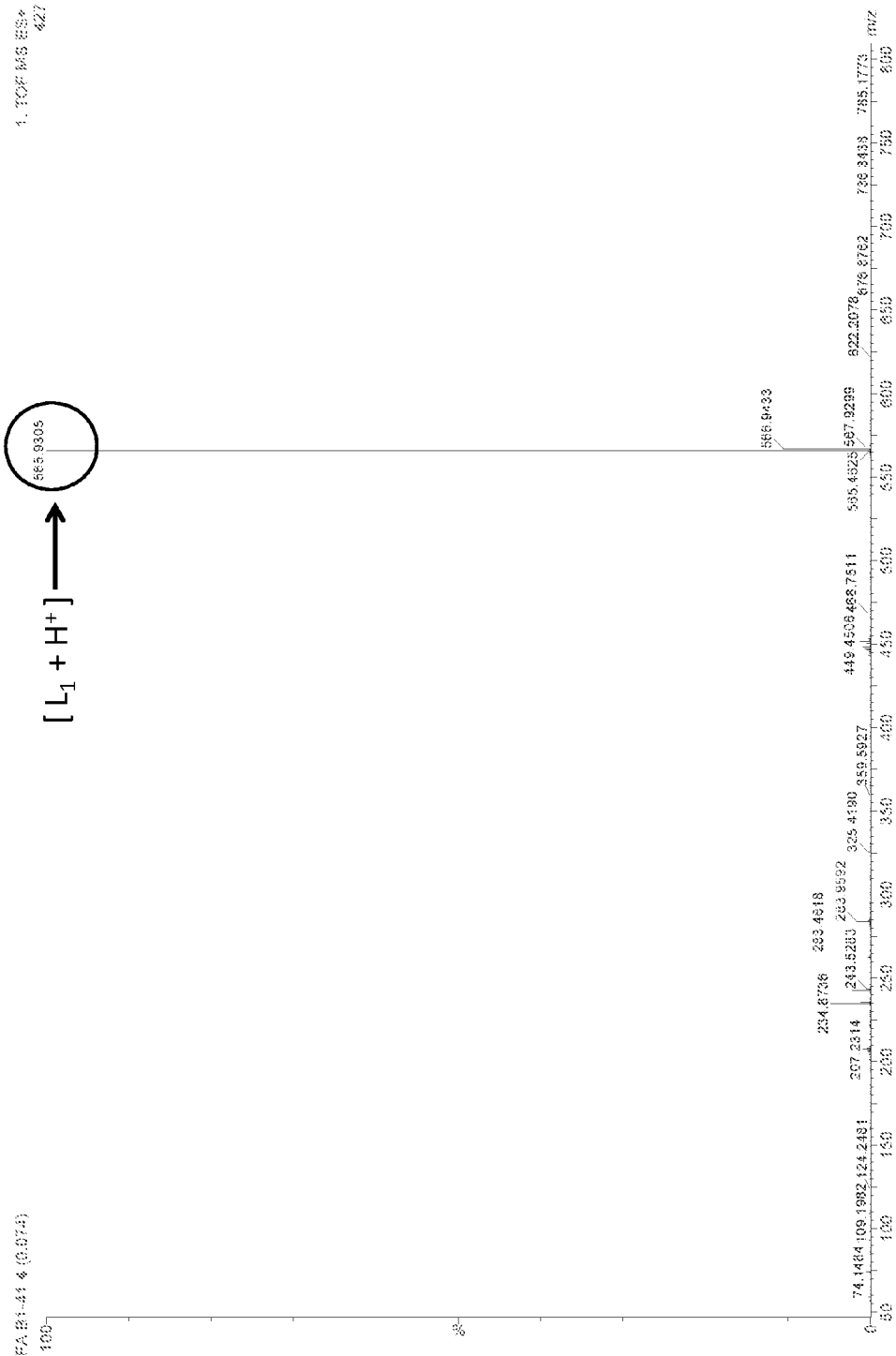
FIG. 3 depicts Mass Spectrum of $L_1$

For calculating the binding affinity of ligand $L_1$ ($1.59 \times 10^{-5}$ M) towards $Cr^{3+}$ in aqueous solution, systematic absorption and emission spectral titration is performed in 0.32 mM Triton X 100 in tris buffer (5 mM, 25 mM NaCl) medium at PH 7.2. The association constant ($K_{abs}$) of $2.4 \times 10^3$ $M^{-1}$ for the $L_1$-$Cr^{3+}$ formation is evaluated from the absorption titration and B-H plot data (FIG. 3). A good linear fit data supported the 1:1 binding stoichiometry. For emission titration, a significant increase in emission intensity at 583 nm is observed with an increase in concentration of $Cr^{3+}$ in aqueous medium. The binding affinity towards $Cr^{3+}$ is also evaluated from linear fit B-H plot for 1:1 stoichiometry and is found to be $2.83 \times 10^3$ $M^{-1}$. The 1:1 binding stoichiometry is further confirmed from Jobs plot and presence of signal for m/z at 616.87 (Calc 616.75) in FAB-MS analysis of a mixture of $L_1$ ($1.59 \times 10-5$ M) and ($9.5 \times 10^{-5}$ M) $Cr(ClO_4)_3$ for $[L_1+Cr^{3+}]$.

To understand the role of Triton X 100 surfactant in the sensing of $Cr^{3+}$, the emission intensity of receptor $L_1$ ($1.59 \times 10^{-5}$ M) in presence of aqueous $Cr^{3+}$ (5 mole eqv.) solution was plotted against different concentration of Triton X 100. The figure shows that sensing efficiency of the reagent described above is maximum when [Triton X]=0.4 mM. This is also a good agreement with the data obtained from photo physical study shown in table below. Thus the surfactant concentration is adjusted to achieve maximum sensing efficiency of receptor $L_1$.

TABLE

Effect of Triton X 100 on binding affinity of $L_1$ to $Cr^{3+}$ in aqueous medium.

| [Titron X 100] (mM) | Binding Constant ($M^{-1}$) | | Quantum yield in water w.r.t. Rhodamine B |
|---|---|---|---|
| | Uv-Vis Spectroscopic Method | Fluorescence Spectroscopic Method | |
| 0.23 | $1.96 \times 10^3$ | $2.0 \times 10^3$ | 0.185 |
| 0.32 | $2.4 \times 10^3$ | $2.83 \times 10^3$ | 0.211 |
| 0.4 | $3.2 \times 10^3$ | $3.25 \times 10^3$ | 0.22 |

UV-Vis and Fluorescence Studies:

A solution of the perchlorate salts of the respective ion ($Li^+$, $Na^+$, $K^+$, $Cs^+$, $Ca^{2+}$, $Mg^{2+}$, $Ba^{2+}$, $Sr^{2+}$, $Fe^{2+}$, $Ni^{2+}$, $Co^{2+}$, $Cu^{2+}$, $Mn^{2+}$, $Cd^{2+}$, $Pb^{2+}$, $Ba^{2+}$, $Zn^{2+}$, $Sr^{2+}$, $Hg^{2+}$ and $Cr^{3+}$) and nitrate salts of lanthanides ions ($Tb^{3+}$, $Ho^{3+}$, $Ce^{3+}$, $Sm^{3+}$, $Rb^+$, $Pr^{3+}$, $Eu^{3+}$, $Gd^{3+}$, $Nd^{3+}$, $Dy^{3+}$, $Tm^{3+}$, $Er^{3+}$, $Yb^{3+}$) in pure aqueous medium were used for all studies. The effective final concentrations of all metal salts were maintained at $1.62 \times 10^{-4}$ M.

A stock solution of the receptor $L_1$ ($6.9 \times 10^{-4}$ M) was prepared in acetonitrile medium and 57 μL of this stock solution was added to 2.5 ml of 0.4 mM TX100 in Tris-HCL aqueous buffer medium having solution pH 7.2 to make the effective ligand concentration of $1.59 \times 10^{-5}$ M. The solution was used for all the photophysical studies. $Cr^{3+}$ stock solution ($4.75 \times 10^{-3}$ M) was prepared in pure aqueous medium and was used for all studies. Emission titrations were also performed as a function of [TX100](0.1 mM, 0.23 mM, 0.32 mM, 0.4 mM, 0.6 mM) in Tris-HCl buffer medium of pH 7.2 by monitoring the increase in emission intensity (using $\lambda_{Ext}=530$ nm, $\lambda_{Mon}=583$ nm and slit width 2/2 nm) on binding of $L_1$ to $Cr^{3+}$ for optimizing the maximum enhancement of the emission intensity. The relative fluorescence quantum yields (t) were estimated using equation 1 for different concentration of TX100 (0.1 mM, 0.23 mM, 0.32 mM, 0.4 mM, 0.6 mM) in Tris-HCl buffer medium (having solution pH of 7.2) and by using the Rhodamine B ($\phi_f=0.3$ in aqueous medium at RT) as a reference.

$$\phi_f = \phi_f'(I_{sample}/I_{std})(A_{std}/A_{sample})(\eta^2_{sample}/\eta^2_{std}) \quad \text{Eq. 1}$$

where, $\phi_f'$ was the absolute quantum yield for the rhodamine B and was used as reference; $I_{sample}$ and $I_{std}$ are the integrated emission intensities; $A_{sample}$ and $A_{std}$ are the absorbances at the excitation wavelength, and $\eta_{sample}$ and $\eta_{std}$ are the respective refractive indices.

Computational Methodology:

The geometry of the compounds of Formula-I with chromium ion was examined by using known theories. The optimized geometry shows that the $Cr^{3+}$ ion is coordinated with two nitrogen atoms, one oxygen atom, two olefinic n-bonds and a water molecule.

Figure 11:
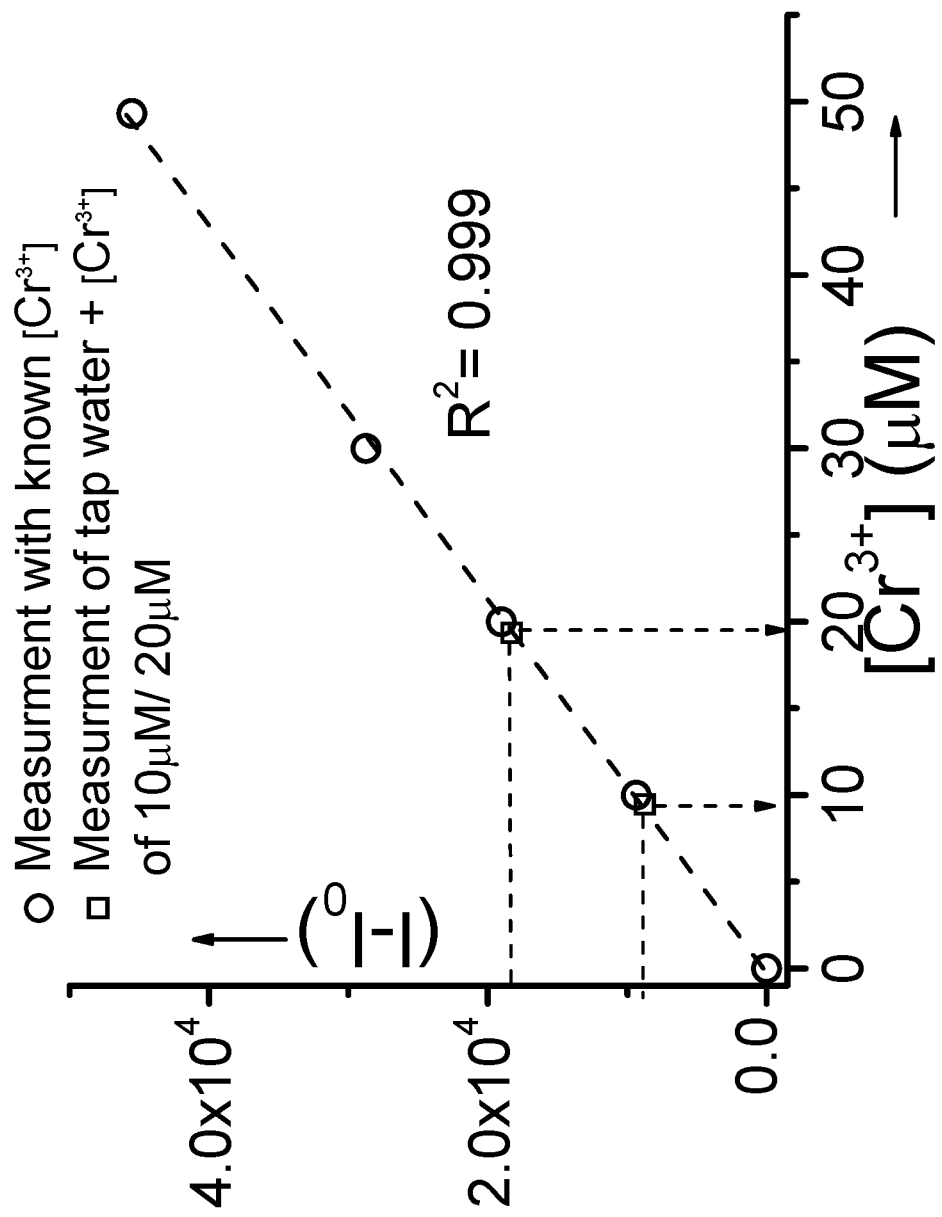
FIG. 11: Plot of (I-I0) vs. [Cr3+], where I0 and I are emission intensities at 583 nm of receptor L1 in the absence and presence of known [Cr3+] as well in tap water spiked with a known amount of Cr3+.

According to the invention, FIG. 11 shows that among all the metal cations, only in the presence of Cr(III), respective absorption and emission (with $\lambda_{Ext}=530$ nm) spectral bands at 562 nm and 583 nm were observed.

Formation of $Cr^{3+}.L_1$ was also confirmed from the result "Formation of Cr3+.L1 was also confirmed from the result of FAB MS study. Signal at m/z value of 616.87 (Calc 616.75) for Cr3+.L1". Affinity of $L_1$ towards Cr(III) and the associated binding constant for the formation of $Cr^{3+}.L_1$ in aq. buffer medium (pH=7.2) was evaluated from the data obtained from B-H plots of the systematic absorption ($K_a^{Abs}=3.2\pm0.2)\cdot10^3$ $M^{-1}$) as well as emission ($K_a^{Ems}=(3.3\pm0.2)\cdot10^3$ $M^{-1}$) spectral titrations.

To envisage the adverse role of high solvation enthalpy of Cr(III) in aqueous medium, similar Uv-vis and emission titrations were carried out in acetonitrile medium using ($[Cr(III)]=(0-1.93\times10^{-4})$M; and $[L_1]=(1.59\times10^{-5}$ M) in $CH_3CN$) and the evaluated formation constant for $Cr^{3+}.L_1$ in acetonitrile was ($K_a^{Abs}=(1.1\pm0.03)\cdot10^6$ $M^{-1}$, $K_a^{Ems}=(1.0\pm0.02)\cdot10^6$ $M^{-1}$ using $\lambda_{Ext}$: 530 nm and $\lambda_{Mon}$: 583 nm for emission titration). The binding affinity of $L_1$ towards $Cr^{3+}$ was evaluated as $K_a^{ITC}=(1.6\pm0.02)\cdot10^6$ $M^{-1}$ in acetonitrile medium at 25° C. using ITC experiments. Comparison of the binding constants evaluated in pure aq. buffer medium and in acetonitrile clearly revealed the energy barrier imposed due to the unfavourable solvation of $Cr^{3+}$ in aqueous medium and thus adversely affecting the affinity of $L_1$ towards $Cr^{3+}$. Thermodynamic parameters were obtained from ITC studies ($\Delta G$ (−(8.48±0.02) kcal $mol^{-1}$), $\Delta H$ ((−20.8±0.4) kcal $mol^{-1}$) and $\Delta S$ (−41.4±0.05) cal $mol^{-1}$) (all symbols are used according to standard terminology). The higher −$\Delta H$ value revealed that binding was exclusively driven by enthalpy change; while small but negative entropy of binding supported the formation of the adduct $Cr^{3+}.L_1$.

FTIR Analysis:

FTIR spectra recorded for $L_1$ and $Cr^{3+}.L_1$, also revealed a distinct shift from 1617 $cm^{-1}$ to 1587 $cm^{-1}$ ($\Delta V=30$ $cm^{-1}$) for C=C stretching frequency. Blue shift in absorption of vinyl group in the FTIR spectrum on coordination to metal ion is reported earlier. This also supports the involvement of olefins in coordination to Cr(III)-centre and possible mode of binding of $L_1$ to Cr(III) is shown in Scheme 1C. No such shifts were observed either in $^1$H NMR or in FTIR spectra of $L_1$ in presence of certain other metal ions and these metal ions were chosen based on their ability to bind to the model reagent $L_2$.

EXAMPLES

The following examples are given by way of illustration of the working of the invention in actual practice and therefore should not be construed to limit the scope of the present invention.

Example 1

Procedure of Synthesis of Aminoethyl Rhodamine B (L):

Amino ethyl rhodamine B is prepared according to literature (J.-H. Soh, K. M. K. Swamy, S. K. Kim, S. Kim, S.-H. Lee, J. Yoon, Tetrahedron Lett., 2007, 48, 5966).

Rhodamine B (1.0 g, 2.26 mmol) is dissolved in 30 mL of ethanol. It is then heated to 70° C. with constant starring. Then ethylene diamine (3 mL) is added to the reaction medium. It is then allowed to reflux at 75° C. for 12 hour. The solvent is removed under vacuum and is dissolved in diluted HCl. Then to this resulting solution, NaOH solution was added in a drop-wise manner until precipitation is complete. The resulting solution mixture is then filtered, washed with water and is further dried to achieve the desired compound, amino ethyl rhodamine derivative as light red colour solid.

Synthesis of Ligand $L_1$:

Amino ethyl rhodamine B (400 mg, 0.826 mmol) was dissolved in 20 mL dry chloroform. To this $Et_3N$ (3 mL) was added and the resulting solution is kept under $N_2$ atmosphere for 20 minutes. Then Allyl bromide (530 μL, 5.9 mmol) was added into starring solution. It was kept under reflux condition at temp 65° C. with constant stirring for 12 h until all the starting materials are consumed. Then 10 mL of water was added to it. The organic Layer is collected and dried over anhydrous $Na_2SO_4$ before concentration. It was finally purified by column chromatography using silica gel as stationary phase and 10% ethyl acetate in hexane as eluent or mobile phase to isolate $L_1$ in pure form with 50% yield. $^1H$ NMR (500 MHz, $CDCl_3$, $SiMe_4$, J (Hz), δ ppm): 7.80 (d, J=4.6), 7.35-7.30 (m), 6.99 (d, J=4.4), 6.35-6.27 (m), 6.16 (d, J=8.8), 5.56 (td, J=16.5, 6.5), 4.96-4.88 (m), 3.24 (dd, J=13.7, 6.8), 3.18-3.09 (m), 2.85 (d, J=6.2), 2.21-2.13 (m), 1.07 (t, J=6.8). $^{13}C$ NMR (500 MHz, $CDCl_3$, $SiMe_4$, δ ppm): 167.70, 153.38, 148.70, 135.13, 132.22, 131.54, 128.98, 127.97, 123.78, 122.63, 117.53, 108.03, 105.58, 97.73, 64.85, 56.60, 50.46, 44.37, 37.75, 29.69, 12.60. ESI-MS (+ve mode, m/z): 565.93 ($M+H^+$), Calc. for $C_{36}H_{44}N_4O_2$ is 564.76.

Example 2: Synthesis of Ligand $L_2$

Amino ethyl rhodamine B (200 mg, 0.41 mmol) was dissolved in 15 mL dry chloroform. To this $Et_3N$ (500 μL) was added and the resulting solution was stirred for 20 minutes under $N_2$ atmosphere. Then 1-bromopropane (120 μL, 1.35 mmol) was added and the resulting reaction mixture was refluxed at temp for 24 h until all the starting materials were consumed (Checked by TLC at different time interval). After this reaction mixture was allowed to attain the room temperature, 10 mL of water was added. The organic layer, after drying over anhydrous $Na_2SO_4$, was collected and followed by the removal of chloroform under vacuum to yield the crude product. Column chromatography was performed using silica gel as stationary phase and 10% ethyl acetate in hexane as mobile phase for isolating $L_2$ in pure form with 40% yield. $^1H$ NMR (500 MHz, $CDCl_3$, $SiMe_4$, J (Hz), δ ppm): δ 7.81 (dd, 1H, J=5.9, 2.6, $H_{18}$), 7.37 (dd, 2H, J=5.6, 3.0, $H_{16}$, $H_{17}$), 7.05-7.00 (m, 1H, $H_{15}$), 6.35 (s, 1H, $H_{12}$), 6.33 (s, 1H, $H_2$), 6.31 (d, 2H, J=2.5, $H_5$, $H_9$), 6.19 (dd, 2H, J=8.9, 2.6, $H_4$, $H_{10}$), 3.26 (q, 8H, J=7.0, $H_{29}$, $H_{31}$, $H_{33}$, $H_{35}$), 3.09 (d, 2H, J=5.8, $H_{21}$), 2.15 (s, 6H, $H_{22}$, $H_{23}$, $H_{26}$), 1.18 (d, 4H, J=6.7, $H_{24}$, $H_{27}$), 1.09 (t, 12H, J=7.0, $H_{30}$, $H_{32}$, $H_{36}$, $H_{34}$), 0.68 (t, 6H, J=6.8, $H_{25}$, $H_{28}$). $^{13}C$ NMR (125 MHz, $CDCl_3$, $SiMe_4$, δ ppm): 167.75, 153.77, 148.72, 148.25, 132.25, 129.18, 127.78, 123.93, 122.59, 108.48, 105.63, 97.94, 64.95, 56.78, 50.96, 44.34, 37.79, 37.47, 20.27, 12.54, 11.82. IR (KBr): $v_{max}/cm^{-1}$=1680. ESI-MS (+ve mode, m/z): 569.29 ($M+H^+$), Calc. for $C_{36}H_{44}N_4O_2$ is 568.79. Elemental Analysis: Calculated (C, 76.02; H, 8.51; N, 9.85); Experimentally obtained (C, 76.20; H, 8.50; N, 9.88).

Example 3: Solubilization of Ligand $L_1$

Method of Preparation of Ligand ($L_1$) and Solubilization of $L_1$ in Water Using Triton X 100:

Final Ligand ($L_1$) Concentration=$1.59 \times 10^{-5}$ M

Concentration of $Cr^{3+}$ in Aqueous Solution=$10^{-4}$ M

1. Make 10 mL of $7.092 \times 10^{-4}$ M stock solution of ligand $L_1$ in pure HPLC grade acetonitrile (Dissolve 4 mg of ligand $L_1$ in 10 mL HPLC grade acetonitrile).

2. Make a solution of 0.32 mM Triton X 100 in Tris-HCl Buffer (5 mM, 25 mM NaCl, pH 7.2) i.e medium. It is better to make 50 mL Tris-HCL Buffer solution (5 mM tris Buffer, 25 mM NaCl) and adjust the PH to 7.2. Then add 9.34 μL (10 mg) of Triton X 100 to 50 mL of Tris-HCl Buffer (pH 7.2) solution and stir the solution gently for 10 minutes just to homogenies (avoid vigorous shaking).

3. Take exactly 56 μL of ligand stocks solution and add to 2.5 mL of solvent solution (i.e. 0.32 mM Triton X 100 in Tris-HCL buffer solution of pH 7.2) to make $1.59 \times 10^{-5}$ M of ligand ($L_1$) solution for studies.

Molecular weight of the Ligand=564

Molecular weight of the Triton X 100=625

Density of Triton X 100=1.07 g/L

Molecular weight of the Tris buffer=121.14

Example 3

Figure 4:
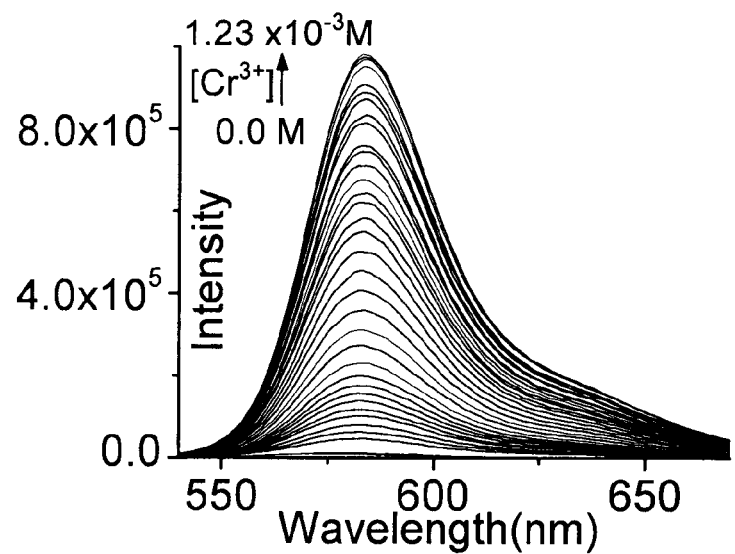
FIG. 4 depicts Emission titration of $L_1$ with aqueous Cr (III) solution in 0.4 mM Triton X in Tris PH 7.2. B-H plot. Binding constant (K)=$2.83 \times 10^3 M^{-1}$.
Figure 6:
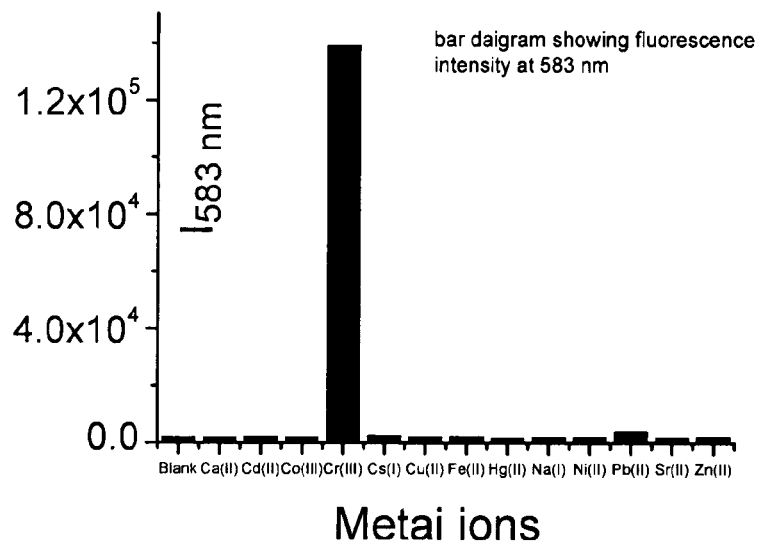
FIG. 6: depicts Bar diagram showing emission change at λ=582 nm upon addition of various metal ions ($1.0 \times 10^{-4}$M) to 15.6 μM of $L_1$ in 0.23 mM Triton X 100 in Tris Buffer PH 7.2.

Method of Detection of Cr(III) from Pure Aqueous Solution $3.28 \times 10^{-3}$ M Cr(III) solution in water is prepared and then it is gradually added to a solution of the ligand $L_1$, where effective ligand concentration is $1.59 \times 10^{-5}$ M in a Tris buffer with solution pH of 7.2 having 0.32 mM Triton X 100. Uv-vis and luminescence spectra are recorded in absence and presence of [Cr(III)]. In emission spectra a 200 fold increase in spectral intensity at 583 nm ($\lambda_{ext}$=530 nm and slit 2/2) is observed, while a simultaneous change in solution colour is observed from colourless to pink red (please refer to FIGS. 4 and 6).

Real Sample Analysis:

To cheeked the applicability of the methods in real sample analysis, probe L1 was applied to detect Cr3+ in tap water. No Cr3+ was obtained in tap water samples. Water samples were collected and pH was adjusted to 7.2 using Tris buffer (10 mM, 25 mM NaCl), spiked with known (10 μM and 20 μM) concentration of Cr3+ and emission spectra was recorded. The result was summarised in Table 1.

TABLE 1

Determination of $Cr^{3+}$ in Tap Water.

| Sample No. | $Cr^{3+}$ Added (μM) | $Cr^{3+}$ Found (μM) | Recovery (%) |
| --- | --- | --- | --- |
| 1 | 10 | 9.81 | 98.1 |
| 2 | 20 | 19.67 | 98.3 |

Advantages of the Invention

1. With this ligand ($L_1$), Cr(III) can be detected from pure aqueous solutions at physiological pH.

2. The ligand can also be used as a colorimetric as well as fluorescent chemosensor for the detection of Cr(III) in aqueous solutions.

3. The use of Triton X 100 to create micro-micellar environment that makes the ligand soluble in water or tri buffer medium having pH 7.2 cell membrane permeable in addition to maximizing the sensing efficiency.

The invention claimed is:

1. A ligand of Formula I (Lx) for detection of Chromium in pure aqueous medium, wherein Formula I (Lx) is:

Formula I

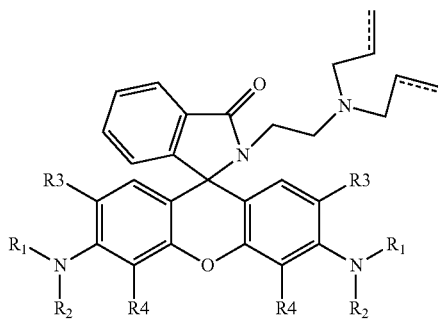

(Lx)

wherein $R_1$ and $R_2$ are same or different and independently selected from the group consisting of H, linear or branched (C1-C6) alkyl, aryl and dansyl; R3 is H or methyl; R4 is H or (C1-C6) alkyl;

wherein R1 may form a saturated or unsaturated, 5- or 6-membered ring with R3 and/or R2 may form a saturated or unsaturated, 5- or 6-membered ring with R4; and ( . . . ) line optionally represents a single bond of a carbon-carbon double bond system.

2. The ligand of Formula I (Lx) according to claim 1, wherein the ligand is a compound selected from the group consisting of:

$L_1$

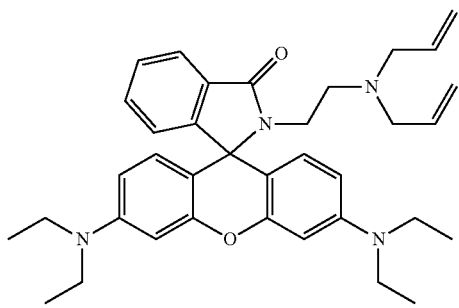

$L_2$

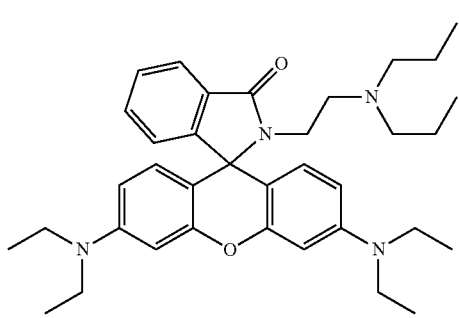

$L_3$

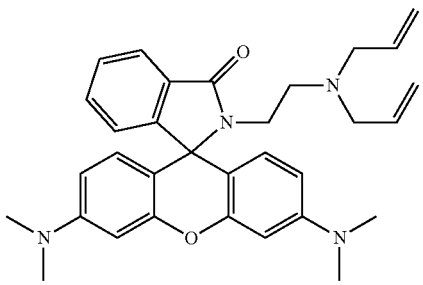

$L_4$

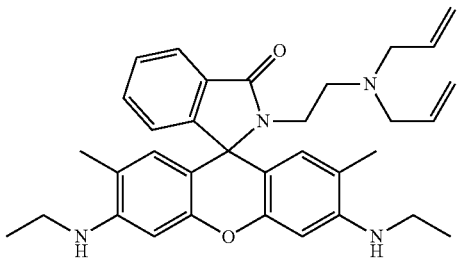

$L_5$

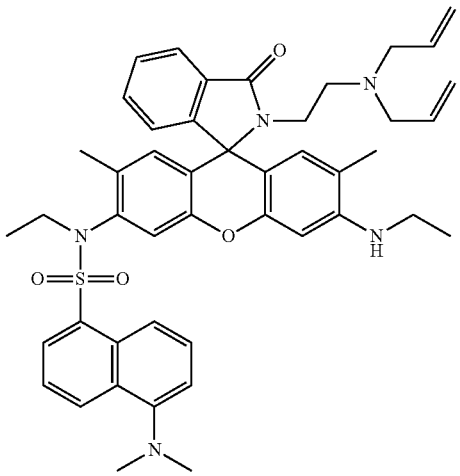

$L_6$

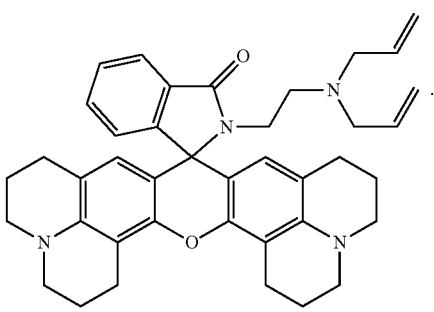

3. A process of preparation of a ligand of Formula I (Lx) according to claim 1, wherein the process comprises:
   a. refluxing ethylene diamine and rhodamine B derivatives (II) in organic solvent, to obtain a corresponding amino ethylene rhodamine derivative (III) and;
   b. refluxing the amino ethylene rhodamine derivative of step (a) in the presence of (A-Br) aliphatic bromide, triethyl amine and dry $CHCl_3$ under inert conditions to obtain the ligand of Formula I (Lx),

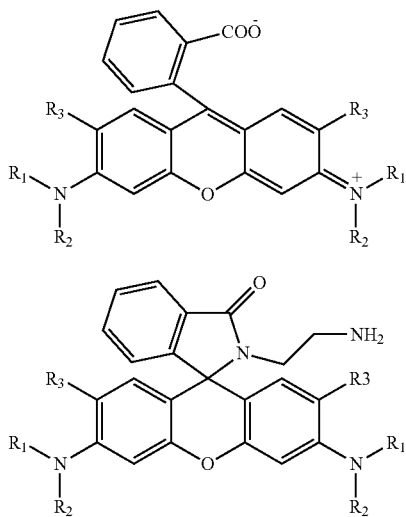

wherein $R_1$ and $R_2$ are same or different and independently selected from the group consisting of H, linear or branched (C1-C6) alkyl, aryl and dansyl; R3 is H or methyl;

wherein R1 may form a saturated or unsaturated, 5- or 6-membered ring with R3.

4. The process according to claim 3, wherein the organic solvent is a polar organic solvent selected from the group consisting of methanol, isopropanol, n-propanol, ethanol, water, butanol and mixtures thereof.

5. The process according to claim 3, wherein the aliphatic bromide (A-Br) is an alkene bromide selected from the group consisting of allyl bromide and 3-bromoprop-1-ene or an alkyl bromide selected from the group consisting of propyl bromide and 1-bromopropane.

6. A process for selective detection of Cr (III) using ligands of Formula I (Lx) according to claim 1, in aqueous medium as well as in physiological liquid of pH (7.2) comprising:
   a. preparing a solution of tris(hydroxymethyl)aminomethane buffer (Tris buffer) and Polyethylene glycol tert-octylphenyl ether (Triton X 100) at pH 7.2;
   b. preparing a stock solution of ligands of Formula I (Lx) in a water miscible solvent in concentration ranges from 6.0 to $8.0 \times 10^{-4}$ M;
   c. mixing the stock solution of step (b) with the solution of step (a) to solubilize the ligand of formula I to form a second solution;
   d. preparing a Chromium (III) metal stock solution using water;
   e. adding the Chromium (III) metal stock solution gradually to the second solution of step (c) to form a third solution; and
   f. recording a spectrum of the third solution in a UV or fluorescence spectrometer.

7. The process for selective detection of Cr (III) according to claim 6, wherein the water miscible solvent is selected from the group consisting of acetonitrile, Methanol, DMSO, Ethanol, THF, DMF and mixtures thereof.

8. A kit for selective detection of Cr (III) using novel ligands of Formula I (Lx) according to claim 1, comprising:
   a) Ligand $L_1$ stock solution ($6.9 \times 10^{-4}$ M) in acetonitrile;
   b) 0.32 mM Triton X 100 in Tris buffer solution at pH 7.2;
   c) Aqueous Cr(III) solution ($3.28 \times 10^{-3}$ M);
   d) Final ligand solution ($1.59 \times 10^{-5}$ M) in 0.32 mM Triton X 100 in Tris buffer having solution pH of 7.2.

* * * * *